US007241622B2

(12) United States Patent
Van Dyck et al.

(10) Patent No.: US 7,241,622 B2
(45) Date of Patent: Jul. 10, 2007

(54) METHOD FOR HIGH THROUGHPUT SCREENING OF ANTIOXIDANTS AT NEAR AMBIENT TEMPERATURES

(75) Inventors: Stefaan Van Dyck, Brasschaat (BE); Waut Dooghe, Lommel (BE); Tom Verleyen, Bazel (BE); Clifford Adams, Antwerp (BE)

(73) Assignee: Kemin Industries, Inc., Des Moines, IA (US)

( * ) Notice: Subject to any disclaimer, the term of this patent is extended or adjusted under 35 U.S.C. 154(b) by 361 days.

(21) Appl. No.: 10/829,792

(22) Filed: Apr. 22, 2004

(65) Prior Publication Data

US 2005/0239208 A1  Oct. 27, 2005

(51) Int. Cl.
*G01N 33/92* (2006.01)
*G01N 33/02* (2006.01)

(52) U.S. Cl. .................. 436/71; 436/20; 436/106; 436/903

(58) Field of Classification Search ............. 436/20, 436/71, 147, 106, 903, 904
See application file for complete search history.

(56) References Cited

U.S. PATENT DOCUMENTS

| | | | |
|---|---|---|---|
| 4,098,575 A | 7/1978 | Matsushita | |
| 4,253,848 A | 3/1981 | Porter | |
| 5,061,633 A | 10/1991 | Meguro | |
| 5,135,850 A | 8/1992 | Prost | |
| 5,339,254 A | 8/1994 | Matlock | |
| 5,463,321 A | 10/1995 | Matlock | |
| 5,712,165 A | 1/1998 | Alvarez | |
| 5,726,063 A | 3/1998 | Gerard-Monnier | |
| 5,912,179 A | 6/1999 | Alvarez | |
| 6,127,185 A | 10/2000 | Melton | |
| 6,372,508 B1 | 4/2002 | Shnizer | |
| 6,535,823 B1 | 3/2003 | McGovern | |
| 2006/0177888 A1* | 8/2006 | Cynshi et al. | ............. 435/25 |

OTHER PUBLICATIONS

Kishida et al. Journal of Agricultural and Food Chemistry, vol. 41, No. 1, Jan. 1993, pp. 1-4.*
Van Dyck et al. Journal of Agricultural and Food Chemistry, vol. 53, , No. 4, 2005, pp. 887-892.*
Rossell, J.B., "Measurement of Rancidity", *Rancidity in Foods*, second ed., J.C. Allen and r.J. Hamilton, Eds., Elsevier Applied Science: London, UK, pp. 23-52.
Liang, C., Schwarzer, K., "Comparison of four accelerated stability methods for lard and tallow with and without antioxidants", J. Am. Oil., Chemistry Soc., 1998, pp. 1441-1443.
Frankel, E.N., "Stability Methods", *Lipid Oxidation*, The Oily Press Ltd., Dundee, Scotland, 1998, vol. 10, pp. 99-114.
Yoshida Y., Niki E., "Oxidation of Methyl Linoleate in Aqueous Dispersions Induced by Copper and Iron", *Arch. Biochem. Biophys.*, 1992, 1, 107-114.
Yoshida, Y., Niki, E., "oxidation of Phosphatidylcholine liposomes in aqueous dispersions induced by copper and iron", *Bull. Chemistry Soc.*, Japan, 1992, pp. 1849-1854.
Jebe, T.A., Matlock, M.G., Sleeter, R.T., "Collaborative study of the oil stability index analysis", *J.Am.Oil*, Chemistry, Soc. 1993, pp. 1055-1061.
Cao, G., Sofic, E., Prior, R.L., "Antioxidant Capapcity of tea an common vegetables", *j.Agric.Food Chem.*, 1996, pp. 3426-3431.
Krasowska, A., Rosiak, D., Szkapiak, K., Lukaszewicz, M., "Chemiluminescence detection of peroxly radicals and comparison of antioxidant activity of phemolic compounds", Curr. Top. Biophys. 2000, pp. 89-95.
Mei, L., McClements, D.J., Decker, E.A., "Lipid Oxidation in Emulsions as Affected by Charge Status of Antioxidants and Emulsion Droplets", *J. Agric. Food. Chem.*, 1999, 47, pp. 2267-2273.
Decker, E.A., Livisay, S.A., Zhou, S., "A Re-evaluation of the Antioxidant Activity of Purified Camosine", *Biochem.*, 2000, pp. 766-770.
Gao, X., Bjork, L., Traikvski, V., Uggla, M., "Evaluation of antioxidant activities of rosehip ethanol extracts in different test systems", *J. Sci. Food Agric.*, 2000, pp. 2021-2027.
Masuda, T., Mizuguchi, S., Tanaka, T., Irtani, K., Takeda, Y., "Isolation and structure determination of new antioxidative ferulic acid glucoside esters from the rhizome of alpinia speciosa, a zingiberaceae plant used in okinawan food culture", *J. Agric. Food. Chem.*, 2000, pp. 1479-1484.
Koga, T., Moro, K., "Matsudo, t., Antioxidative behaviors of 4-hydroxy-2,5-dimethyl-3(2H)-furanone and 4-hydroxy-2(or5)-ethyl-5(or2)-methyl-3(2H)-furnaone against Lipid Peroxidation", *J. Agric. Food. Chem.*, 1998, pp. 946-951.

(Continued)

*Primary Examiner*—Maureen M. Wallenhorst
(74) *Attorney, Agent, or Firm*—Kent A. Herink; Emily E. Harris

(57) ABSTRACT

A method was developed for the screening of antioxidant efficacy in food and feed matrices. The novel method uses radical initiators to accelerate the oxidation process. Consequently the screening of the oxidation process can be performed at significantly lower temperatures compared to the existing methods. The use of initiators improves the correlation between accelerated screening and real shelf life. This resolves an important issue that is frequently raised concerning the applicability of accelerated oxidation tests conducted at high temperatures. Furthermore feed and food products can be analyzed in their original states because lower temperatures have less influence on the product matrix.

15 Claims, 4 Drawing Sheets

OTHER PUBLICATIONS

Raneva, V., Shimasaki, H., Ishida, Y., Ueta, N., Niki, E., "Antioxidative activity of 3,4-Dihydroxyphenylacetic acid and caffeic acid in rat plasma", *Lipids* 2001, pp. 1111-1116.

Dufour, C., Da Silva, E., Potier, P., Queneau, Y., Dangles, O., "Gallic esters of sucrose as efficient radical scavengers in Lipid Peroxidation", *J. Agric. Food Chem.*, 2002, pp. 3425-3430.

March, J., "Carbocations, carbanions, free radicals, carbenes and nitrenes", *Advanced Organic Chemistry*, Third Ed., John Wiley & Sons: Chichester, UK, pp. 141-178.

"Vazo Free radical sources. Properties, uses, storage and handling", DuPont Product Information No. H-58828-1: DuPont Speciality Chemicals, USA, Feb. 1999.

Thomsen, M.K., Jacobsen, C., Skibsted, L.H., "Mechanism of initiation of oxidation in mayommaise enriched with fish oil as studied by electron spin resonance spectroscopy", *Eur.Food Res. Technol.*, 2000, pp. 381-386.

Thomsen, M.K., Kristensen, D., Skibsted, L.H., "Electron spin resonance spectroscopy for determination of the oxidative stability of food lipids", *J. Am. Oil. Chem. Soc.*, 2000, pp. 725-730.

Massaeli, H., Sobrattee, S., Pierce, G.N., "The importance of lipid solubility in antioxidants and free radical generating systems for determining lipoprotein peroxidation", *Free Radic. Biol. Med.*, 1999, pp. 1524-1530.

Noguchi, N., Yamashita, H., Gotoh, N., Yamomoto, Y., Numano, R., Niki, E., "2,2'-Axobis(4-methoxy-2,4-dimethylvaleronitrile), a New lipid-soluble axo initiator: aplication to oxidations of lipids and low-Density Lipoprotein in solution and aqueous dispersions", *Free Radic. Biol. Med.*, 1998, pp. 259-268.

Krainev, A.G., Bigelow, D.J., "Comparison of 2,2;-azobis(2-amidinopropane) hydrochloride (AAPH) and 2,2;-azobis (2,3-dimethylvaleronitrile)(AMVN) as free radical initiators: A spin-trapping study", *J. Chem.Soc. Perkin Trans. 2*, 1996, pp. 747-754.

Frankel, E.N., Meyer, A., "The problems using one-dimensional methods to evaluate multifunctional food an biological antioxidants", *J. Sci. Food. Agric.*, 2000, pp. 1925-1941.

Chen, Q., Shi, H., Ho, C.-T., "Effects of rosemary extracts and major constituents on lipid oxidation and soybean lipoxygenase activity", *J. Am; Oil Chem. Soc.*, 1992, pp. 999-1002.

Eriksson, C.E., "Lipid oxidation catalysts and inhibitors in raw materials and in processed foods", *Food Chem.*, 1982, pp. 3-19.

Gordon, M.H., Mursi, E., "A Comparison of oil stability based on the metrohm rancimat with stroage at 20 C", *j. am. Oil. Chem.*, 1994, pp. 649-651.

Tian, K., Dasgupta, P.K., Shermer, W.D., "Determination of oxidative stability of lipids in solid samples", *J. Am. Oil Chem. Soc.*, 2000, pp. 217-222.

DuPont Vazo Free Radical Sources, DuPont Product Information No. H-58828-1: DuPont Specialty Chemicals, USA, Feb. 1999, pp. 1-14.

\* cited by examiner

Minor contributor

METHOD FOR HIGH THROUGHPUT SCREENING OF ANTIOXIDANTS AT NEAR AMBIENT TEMPERATURES

BACKGROUND OF THE INVENTION

1. Field of the Invention

The invention relates generally to a method of screening the activity of antioxidant compounds and, more particularly, to a high throughput method for screening the activity of antioxidant compounds at ambient temperatures to more accurately determine antioxidant activity in actual use.

2. Background of Related Art

Antioxidant research is a time-consuming activity when protected samples are evaluated under normal storage conditions. Oxidation at room temperature or below is relatively slow. The signs of emerging rancidity typically only appear after several weeks or even months. For an efficient evaluation of antioxidant systems faster methods of analysis are needed. Many accelerated methods such as Oxidative Stability Instrument (Omnion Inc. Illinois, USA) or OSI, oxygen bomb and Rancimat (Metrohm, CH) use increased temperature to initiate and accelerate the oxidation process. The relation between the rate of any chemical reaction (including oxidation) and temperature can be illustrated using the Arrhenius equation:

$$k = Ae^{\frac{-E_A}{RT}} \quad (1)$$

where k is the rate constant, A is the frequency factor, e is the mathematical constant, $E_A$ is the activation energy, and R is the gas constant. The complete term $$e^{\frac{-E_A}{RT}} \quad (2)$$

counts for the fraction of molecules present in a gas that have energies equal to or in excess of activation energy at a particular temperature. The frequency factor A includes the frequency of collisions and their orientation. This last parameter varies with temperature, although not much. It can be taken as constant across small temperature ranges.

It is possible to calculate what happens to a chemical reaction when the temperature is increased by 10° C., for example from 20 to 30° C. (293 K to 303 K). Because the frequency factor A can be considered constant for this small temperature change, it is only necessary to calculate how equation (2) changes due to the increased temperature. For a typical activation energy of 50 kJ/mol, the following results are obtained:

For 293 K: $e^{\frac{-50,000}{8.31*293}} = 1.21 \cdot 10^{-9}$

For 303 K: $e^{\frac{-50,000}{8.31*303}} = 2.38 \cdot 10^{-9}$

These calculations show that the fraction of the molecules able to react has almost doubled by increasing the temperature by 10° C. This causes the rate of reaction to almost double. This is the merit of this rule-of-thumb often used in simple reaction rate work. As for most simple rules it is only an approximation and therefore should be used with great care for the estimation of shelf life. There are a few other important disadvantages to the use of accelerated oxidation at high temperatures:

First of all, there are limitations to the applicability of Arrhenius' law. The rate constant increases as the temperature goes up, but the rate of increase falls off quite rapidly at higher temperatures. This means that there is no linear correlation between tests at higher temperatures and the actual storage temperature. Also the reaction mechanism of the oxidation process typically changes at higher temperature. Consequently the activation energy of the new mechanism probably will be different, and the linear correlation is lost (Frankel, E. N. Stability methods. In Lipid Oxidation; The Oily Press Ltd: Dundee, Scotland; 1998, Vol. 10, pp. 99-114).

Secondly the high temperature of analysis may change the food or feed matrix. Emulsions can break easily, fats will melt, proteins will denature and coagulate (e.g., meat will be cooked), and water may evaporate out of the product. All these transitions can change the matrix considerably and therefore have a dramatic effect on the correlation of the analysis with the shelf life of the original product.

The analysis of more volatile antioxidants is difficult at high temperatures because an unknown amount of antioxidant activity can be lost during the measurement.

Besides increased temperature it is also possible to use metal ions to increase the oxidation rate (Yoshida, Y.; Niki, E. Oxidation of Methyl Linoleate in Aqueous Dispersions Induced by Copper and Iron. Arch. Biochem. Biophys. 1992, 1, 107-114; Yoshida, Y.; Niki, E. Oxidation of Phosphatidylcholine Liposomes in Aqueous Dispersions Induced by Copper and Iron. Bull. Chem. Soc. Jpn. 1992, 1849-1854). Obviously this is not an option for antioxidant research because a high level of metal ions interferes with chelators present in formulations and therefore gives erroneous results.

There is a need, therefore, for new methods for initiating and accelerating oxidation at low temperatures.

SUMMARY OF THE INVENTION

The present invention discloses the application of diazo-type free radical sources (free radical sources) as initiators and accelerators for oxidation reactions in protected and unprotected substrates, particularly human food and animal feed products. The diazo-type free radical sources are added to the substrates in an amount between about 0.01 and about 2 percent by weight of the substrate, and preferably between about 0.1 and 1 percent by weight of the substrate. Upon gentle heating, these diazo-compounds decompose and form two free radicals. The free radicals react with both mono- and polyunsaturated fatty acid moieties in the substrates to accelerate the generation of lipid radicals. The lipid oxidation process is, accordingly, initiated and accelerated at temperatures that are much lower than in existing methodologies, that is from between about 20° C. and about 70° C. By initiating and accelerating the lipid oxidation processes at lower temperatures, the efficacy of antioxidants is evaluated on the substrates under conditions which are much closer to the actual storage conditions of interest.

An object of the present invention is to provide a method for initiating and accelerating lipid oxidations processes in substrates at lower temperature than is used in existing processes.

Another object of the invention is to provide a method for measuring the efficacy of lipid oxidation protective compounds or antioxidants on a variety of substrates at lower temperatures but over the same time period that are used in existing methods.

A further object of the invention is to provide a method for measuring the efficacy of antioxidants on a variety of substrates under conditions that result in fewer changes to the substrates than is used in existing processes.

DETAILED DESCRIPTION OF PREFERRED EMBODIMENTS

Figure 1:
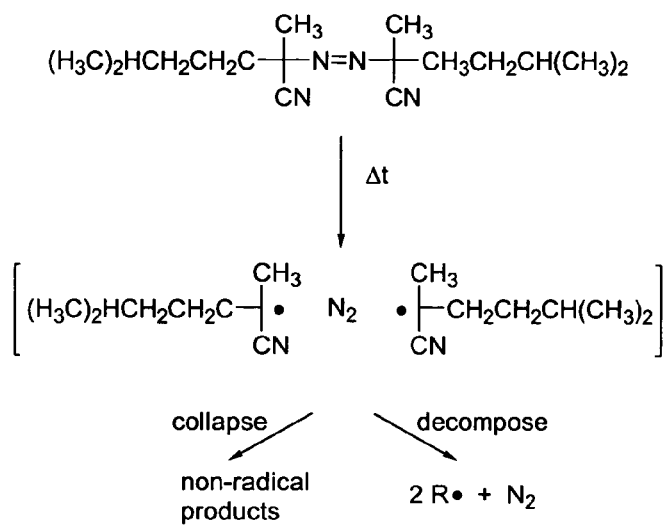
FIG. 1 is a diagram of the decomposition reaction of azo-initiators.

The present invention discloses the application of apolar radical initiators, including specifically diazo-type free radical sources as initiators and accelerators for oxidation reactions. Examples of these compounds include 2,2'-azobis(2,4-dimethylpentanenitrile) (which is sometimes also referred to as 2,2'-azobis(2,4-dimethylpentanitrile) and/or as 2,2'-azobis(2,4-dimethylvaleronitrile) which is abbreviated as AMVN), 2,2-azobis(2,4-dimethylpropanenitrile), and 2,2'-azobis(2,4-dimethylbutanenitrile). Also included would be a modification of the carbon chain attached to the diazo group of these molecules to comprise allylic groups, such as propyl, butyl, pentyl, hexyl, and so on, as well as branched chains, such as isopropyl, 2-methyl butyl, cyclopentyl, and the like. Other groups may also be allowed provided that they do not render the molecule too polar; for example, the addition of an ether group (methoxy), a halogen, and the like, but not carboxylic acids groups or salts (for example, a protonated amine, $NH_3^+$). The application of these compounds overcomes certain issues that are often encountered in the study of antioxidant performance in food or feed products. In solution, these diazo-compounds decompose on gentle heating, liberating one molecule of nitrogen and simultaneously forming two free radicals (FIG. 1).

The stability sequence of alkyl radicals is determined by hyperconjugation and explains that radical stability increases in the order: phenyl<primary (1°)<secondary (2°) <tertiary (3°)<allyl/benzyl (March, J. Carbocations, Carbanions, Free Radicals, Carbenes and Nitrenes. In Advanced Organic Chemistry, Third Edition; John Wiley & Sons: Chichester, UK, 141-178). The poor stability of phenyl radicals, $C_6H_5$, may in turn be attributed to the different hybridization state of the carbon bearing the unpaired electron (sp2 vs. sp3). When a free radical center is flanked by a π-system, a resonance interaction occurs between the p-orbital on the central carbon and the p-orbitals of the π-bond. Resonance stabilization makes such a radical thermodynamically more stable and therefore favors the formation of allyl radicals from alkyl radicals.

Figure 2:
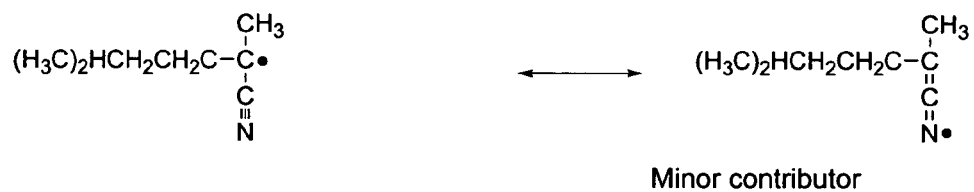
FIG. 2 is a diagram of the resonance stabilization of the 2,4-dimethylpentanenitrile radical.
Figure 3:
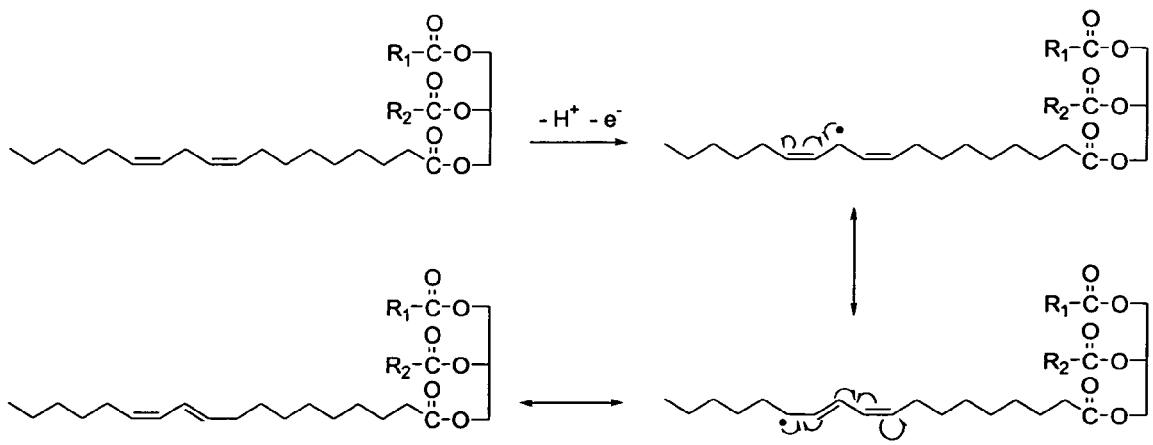
FIG. 3 is a diagram of the resonance stabilization of a lipid radical containing a linoleic moiety.

The radicals formed using this type of substituted azo free radical sources are stabilized in a resonance system including the π-electrons of the cyano group (FIG. 2). Because there is only one possible resonance structure, it is thermodynamically less stable compared to a radical of a polyunsaturated lipid (FIG. 3). Furthermore, radicals from monounsaturated lipids are formed preferentially because they are thermodynamically more stable then the initial 2,4-dimethylpentanenitrile radical (sometimes also referred to as the 2,4-dimethylvaleronitrile radical). The resonance stabilization of the 2,4-dimethylpentanenitrile includes a contributor with the radical on the more electronegative nitrogen atom of the cyano group, which is unfavorable. When the free radical is positioned on an electronegative element, the corresponding resonance structure will only have a very low contribution. Consequently the 2,4-dimethylpentanenitrile radical, or its corresponding peroxyl radical will react immediately with both mono- and polyunsaturated fatty acid moieties because these have more stable resonance contributors. This propagation reaction accelerates the generation of the lipid radicals that are of interest in lipid oxidation studies and hence accelerates the lipid oxidation process at temperatures that are much lower than in existing methodologies. It is also important that the free radical generation occurs at relatively low temperatures to avoid a massive flux of radicals in the lipid system which would impair the validity of the model system for oxidation. All reactive products need enough time to migrate, branch or proceed to other reactions. On the other hand, radical reactions proceed very fast and therefore it may be expected that an increase in oxidation rate by one or two orders of magnitude will not have a dramatic effect on the validity of the method.

Figure 4:
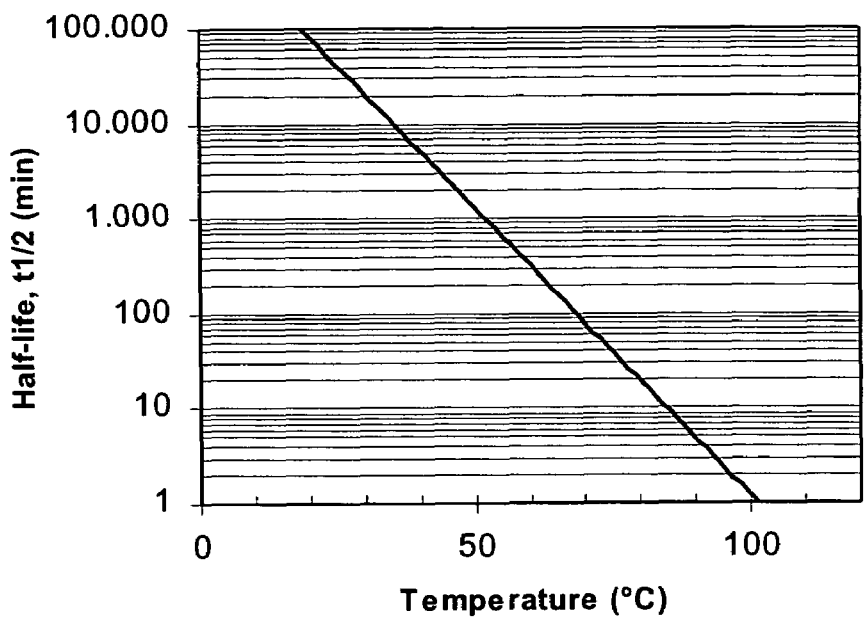
FIG. 4 is a chart of the half-lives for 2,2'-azobis(2,4-dimethylpentanenitrile).

Because the decomposition is first-order, the rate of free-radical formation is dependent on the temperature. The half-lives for 2,2'-azobis(2,4-dimethylpentanenitrile) (Vazo® 52) are given in FIG. 4 (Anonymous, Vazo Free Radical Sources. Properties, Uses, Storage, and Handling, in DuPont Product information no.: H-58828-1: DuPont Specialty Chemicals, USA).

The free radical initiators are added to the substrate in an amount between about 0.01% and about 2% by weight, and preferably between about 0.05% and about 1% by weight.

The assay is carried out at a temperature between about 20° C. and about 70° C., and preferably between about 35° C. and about 60° C.

NOMENCLATURE

In order to distinguish this novel method from other accelerated tests an adapted nomenclature is used: Analyses that are accelerated using a free radical source instead of heat are classified as 'Free Radical Generation assays' or in short 'FRG assays'. Depending on the method to detect oxidation, combinations comparable to hyphenated analytical techniques are used. For example, FRG-OSI is used when the oxidation is measured through increase of conductivity as in the oxidative stability instrument, and FRG- OB is used when the pressure in the headspace is measured as in the oxygen bomb. Combinations with other techniques are assigned accordingly.

MATERIALS AND METHODS

Chemicals: A sample of Vazo® 52 or 2,2'-azobis(2,4-dimethylpentanenitrile) was obtained from DuPont Luxemburg. Vazo® 64 or 2,2-azobis(2,4-dimethylpropanenitrile) and Vazo® 67 or 2,2'-azobis(2,4-dimethylbutanenitrile) were purchased from Aldrich.

Sample matrices: Refined soybean oil (Vandemoortele, Belgium) was purchased at a local supermarket. Refined poultry fat was obtained from Claessen, Ravels, Belgium. Mayonnaise samples were produced using the following recipe: a mixture is prepared using 8.4 g of sugar, 6.0 g or salt and, if included, the antioxidant; 4 egg yolks are blended with 10 g or mustard and 30 g of vinegar; when a homogenous mass is obtained, the sugar mixture is added and mixed again; next, 436 g of rapeseed oil is added, starting with 4 g, followed by thorough blending; the process of adding oil and blending is repeated using twice the amount of oil in each succeeding step. Table 1 shows the peroxide values of the lipids used in this study.

TABLE 1

Peroxide values of the used lipids

| Lipid type | PV (meq/kg) |
|---|---|
| soybean oil | 2.27 |
| poultry fat | 3.27 |
| Mayonnaise[1] | 0.857 |

[1]The PV value of the rapeseed oil used was 1.076

Treatments and preparation: For the addition of Vazo free radical sources to oils, fats or emulsions, the initiator is gently ground in a mortar in the fume hood; mechanical grinding is unsuitable because of the liberation of excess heat. The ground material is added to the oil, fat or emulsion, which is then heated to about 40° C. The samples are magnetically stirred for a time that is typically about 15 to 30 minutes, but this may vary depending on the matrix. Because the oxidation process already starts upon the first addition of the initiator, care should be taken that all samples are heated for the same amount of time. Alternatively, the initiator can be put on a suitable carrier: First, the initiator is dissolved in a suitable solvent (see the manufacturer's list of solvents in Anonymous, Vazo Free Radical Sources. Properties, Uses, Storage, and Handling, in DuPont Product information no.: H-58828-1: DuPont Specialty Chemicals, USA; preferred solvents have a polarity that allows good solution of the free radical inititator and has a low boiling point so that it is easy to remove, such as acetone or ethyl acetate, although many others can be used provided they do not create a toxicity concern, such as benzene, chloroform, or the like), and next the solution is mixed with a suitable carrier (the carrier is preferably chemically inert, is fine to allow good dispersion in the substrate, and can absorb the liquid present in the initiator; a preferred carrier is silica gel, but other silicates, clays, and zeolites may be used provided they do not introduce pro-oxidant metal ions into the substrate). The composition is dried in the air at ambient temperatures and then preferably stored at 10° C. or below. A powder is obtained that distributes very easily in a wide variety of samples.

In order to add the initiator to meat, the initiator is also ground in a mortar and mixed directly with the meat. Once the initiator is diluted in the meat it is safe to use additional mechanical blending.

Dose response and reproducibility studies on soybean oil in FRG-OSI were performed on various samples, each prepared in triplicate (n=3) and included either (1) 0.4% Vazo 52, (2) 0.6% Vazo 52, or (3) 0.8% Vazo 52. Preparation of the samples was performed according to the above method.

Analytical: The oxidative status of the lipids was monitored by a combination of analytical methods. Oxidative stability of the soybean oil samples was determined by OSI (Oxidative Stability Instrument, Omnion, Rockland, Mass.). The procedure was carried out according to the AOCS Official Method Cd 12$b$-92 at the indicated temperature. Primary oxidation products were determined by the peroxide value according to the analytical method following:

A starch indicator solution comprising a saturated solution of KI is prepared by dissolving 30 g+1 g KI p.a. in 20 ml±1 ml de-ionized water; the presence of undissolved crystals indicates the solution is saturated. A 0.0100 M solution of $KIO_3$ is prepared by dissolving 0.2140 g±0.0001 g $KIO_3$ in de-ionized water followed by dilution to 100 ml in a volumetric flask. A standardized sodium thiosulfate solution is prepared as follows: Pipette 10 ml of the $KIO_3$ solution in an Erlenmeyer flask; add 2 g±0.1 g KI and shake; add approximately 2 ml HCl 6N (dissolve 18.5 ml+0.5 ml HCl p.a. (min. 37%) in de-ionized water and dilute to 100 ml in a volumetric flask); titrate immediately with $Na_2S_2O_3$ 0.01N until the solution becomes pale yellow; add 1 to 2 ml starch indicator; and titrate slowly until a colorless solution is obtained.

One gram±0.01 g fat or oil is weighed and added in an Erlenmeyer flask or in a 50 ml beaker. Thirty ml±1 ml acetic acid-methylene chloride mixture (Acetic acid p.a./methylene chloride p.a. 3:2 (v/v)) is added. The flask or beaker is shaken until the fat or oil is completely dissolved. Five-hundred µl saturated KI solution and the beaker or flask is intensely shaken and the solution is allowed to react for about 1 minute. Thirty ml±1 ml de-ionized water is added. Titrate slowly with sodium thiosulfate ($Na_2S_2O_3$ 0.01N) while shaking constantly and intensely to release all the iodine out of the methylene chloride layer. Titrate until the brown iodine becomes pale yellow. Add 1 to 2 ml starch solution. Titrate further with $Na_2S_2O_3$ 0.01 N slowly until the blue color has just disappeared.

Peroxide values expressed as milli equivalents peroxides per 1000 g sample are determined by the formula:

$$\frac{ml\ Na_2S_2O_3 \times NNa_2S_2O_3 \times 1000}{g\ sample}$$

Experimental design and analysis: Data were analyzed by analysis of variance using Microsoft Excel Analysis Toolpak and Graphpad Instat 2.0 software.

RESULTS

Experiment 1—Selection of a Suitable Initiator

Figure 5:
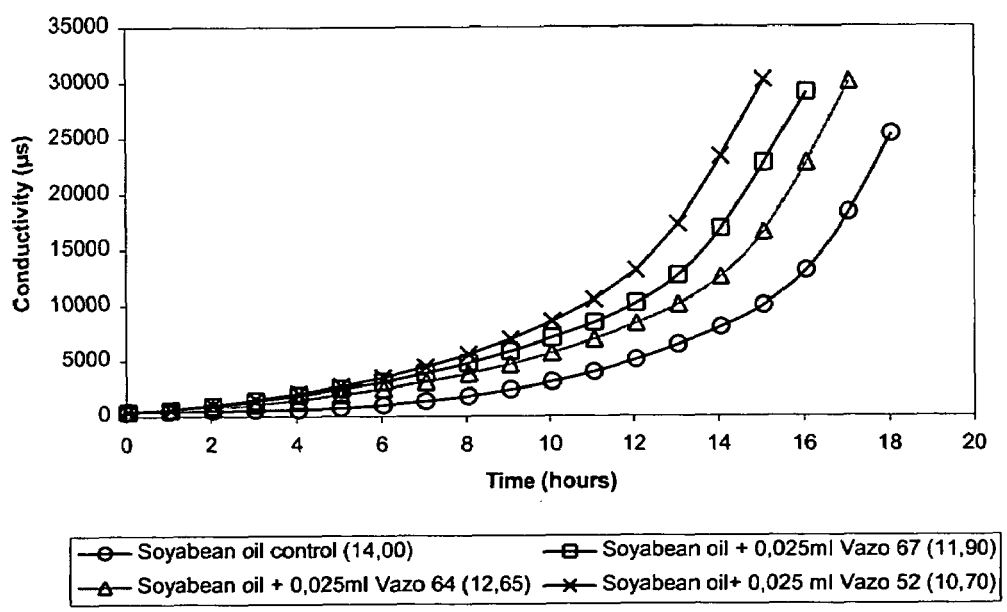
FIG. 5 is a chart of the acceleration of oxidation with different free radical sources evaluated using the Oxidative Stability Instrument (OSI) method at 98° C.

In a first experiment three different oil-soluble free radical sources were compared in order to identify the most efficient initiator of oxidation. Water-soluble initiators are available but were not included in the test since they react very differently. A water soluble initiator will spend the longest part of its lifetime in the water phase of an emulsion. Consequently the radicals produced can participate in many types of reactions that are different from the reactions with lipids. It can be anticipated that this will result in a model that is not very closely related to lipid oxidation. In order to establish the reactivity order of three available diazo-initiators, an ethyl acetate stock solution containing 0.1M of the selected free radical source was prepared. An amount of 0.025 ml of the mixture was mixed with 10 g of soybean oil. The oil samples were analyzed with OSI at 98° C. (FIG. 5). The following order of activity could be established: Vazo® 64<Vazo® 67<Vazo® 52. This order corresponds with the half-life times of these compounds reported by DuPont. Vazo® 52 was selected for further trials because of its superior activity and low toxicity.

Experiment 2—Dose Response and Reproducibility in OSI

After the selection of the most suitable free radical source a trial was initiated to evaluate dose-response and reproducibility. A total of 3 different concentrations of Vazo® 52 (0.4%, 0.6% and 0.8%) were used to accelerate the oxidation of soybean oil at 50° C. All analyses were performed in triplicate. The results in Table 2 show that the oxidation is tremendously accelerated. Normally the OSI for soybean of this type oil at 50° C. can be expected to be about 19 days. The time of analysis in this experiment could be reduced to less than one day.

TABLE 2

Reproducibility of the accelerated oxidation of soybean oil at 50° C.

| Repetition # | Vazo ® 52 (%) | OSI (h) | Average (h) | Standard Deviation (h) | Relative error (%) |
|---|---|---|---|---|---|
| 1 | 0.8 | 22.66 | | | |
| 2 | 0.8 | 22.46 | 22.84 | ±0.49 | ±2.14 |
| 3 | 0.8 | 23.39 | | | |
| 1 | 0.6 | 33.76 | | | |
| 2 | 0.6 | 33.63 | 33.82 | ±0.14 | ±0.41 |
| 3 | 0.6 | 33.48 | | | |
| 1 | 0.4 | 67.30 | | | |
| 2 | 0.4 | 66.00 | 66.42 | ±0.78 | ±1.17 |
| 3 | 0.4 | 65.90 | | | |

Figure 6:
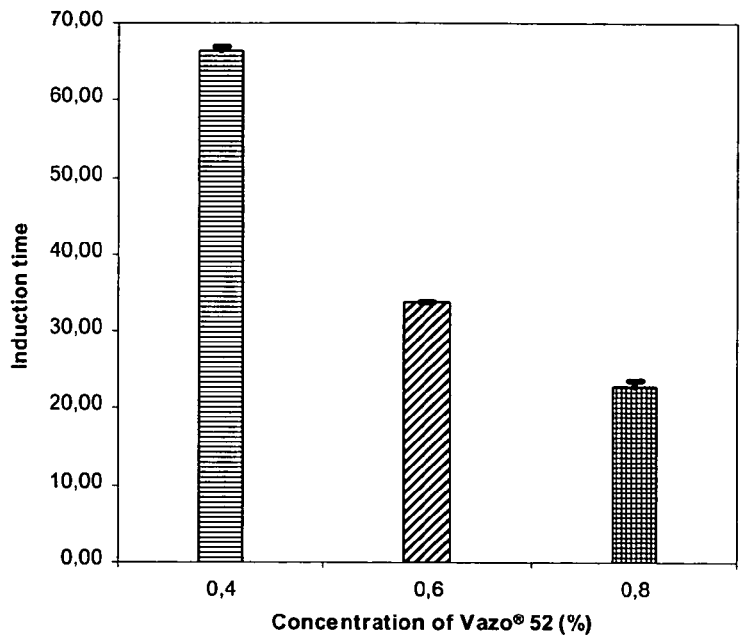
FIG. 6 is a chart of the dose-response for an OSI of soybean oil at 50° C. for different concentrations of 2,2'-azobis(2,4-dimethylpentanenitrile).

The dose-response relation described in FIG. 6 shows that the correlation between the free radical source concentration and induction time is not linear. In this case the curve starts to even out around 0.8% of the initiator. This concentration is still practical in use because solubility of the initiator is not an issue at a level of 0.8%. Higher concentrations will not yield an important decrease of the analysis time, but the preparation of the samples will be more demanding and time consuming due to the lower solubility of Vazo® 52 at higher concentrations.

The present method uses OSI merely as a detector of oxidation. Other methods of detection can also be used such as oxygen pressure in the headspace (oxygen bomb or OB), Thiobarbituric Acid Reactive Substances (TBARS), active oxygen method (AOM), peroxide value, and the like.

Experiment 3—Dose Response and Reproducibility in the Oxygen Bomb

Figure 7:
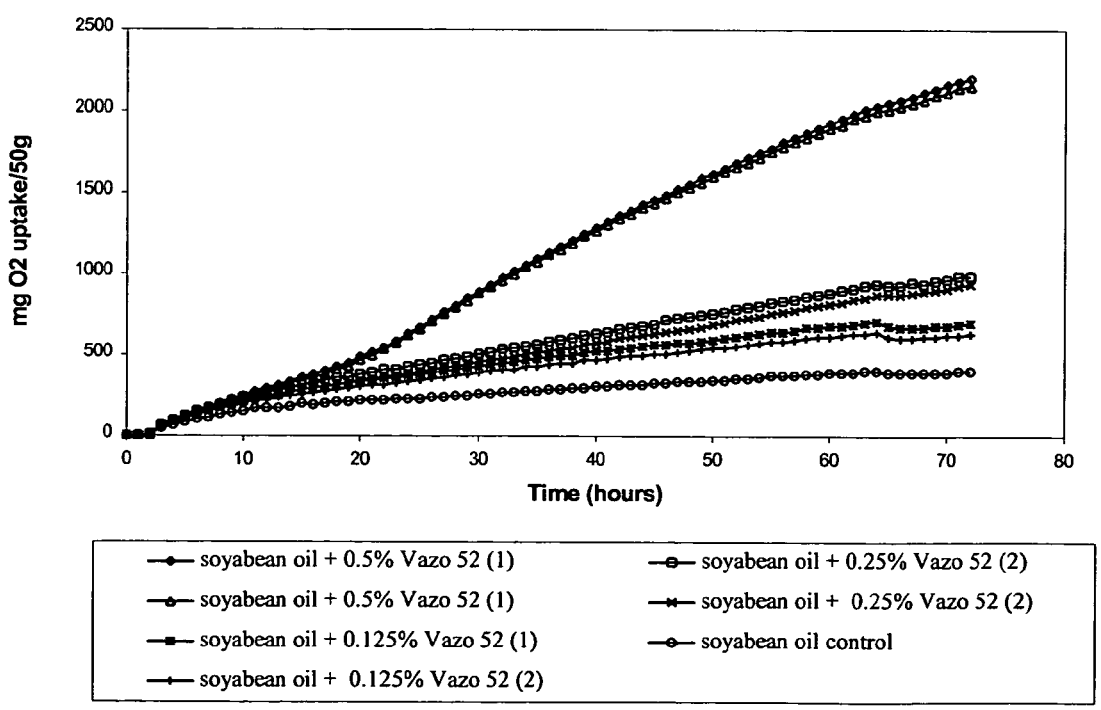
FIG. 7 is a chart of the accelerated oxidation of soybean oil at 50° C. measured with oxygen bomb for different concentrations of 2,2'-azobis(2,4-dimethylpentanenitrile).

In FIG. 7, an example is given of the accelerated oxidation in the oxygen bomb at 50° C. with soybean oil using Vazo® 52. The data show that this new methodology proves to be very reproducible also in the oxygen bomb. Another observation is that the required concentrations of the free radical source are lower than for OSI. The use of a free radical source in combination with high oxygen pressure increases the oxidation rate compared to OSI. This also reflects on the free radical source dosage that is needed to reach an induction point after about 24 hours. For OSI this is 0.8% while for the OB only 0.5% of the initiator is needed.

Experiment 4—Shelf Life Prediction of Antioxidant Treated Mayonnaise

Mayonnaise is a typical example of a matrix that is destroyed during conventional accelerated oxidation studies. The emulsion tends to break at elevated temperatures and the results therefore relate more to the bulk oil liberated from the emulsion during the analysis. Reduction of the temperature of analysis to about 40° C. avoids destruction of the matrix and therefore gives a much more realistic view on the oxidative stability of the emulsion. However, when only mild temperature stress is used without additional initiator only minimal acceleration of oxidation is observed (Thomsen, M. K.; Jacobsen, C.; Skibsted, L. H. Mechanism of Initiation of Oxidation in Mayonnaise Enriched with Fish Oil as Studied by Electron Spin Resonance Spectroscopy. Eur. Food. Res. Technol. 2000, 381-386; Thomsen M. K.; Kristensen, D.; Skibsted, L. H. Electron Spin Resonance Spectroscopy for Determination of the Oxidative Stability of Food Lipids. J. Am. Oil Chem. Soc. 2000, 725-730).

An attempt was made to determine the feasibility of replacing the synthetic antioxidant EDTA, which is commonly used in dressings, with a natural rosemary extract. For this purpose three groups of mayonnaise samples were evaluated with FRG-OB: (1) negative control without antioxidant; (2) positive control with 75 ppm EDTA; and (3) treatment with 750 ppm of Fortium® R20 Liquid brand of a natural extract of rosemary (Kemin Industries, Des Moines, Iowa). Identical samples were produced without initiator and stored at 22° C. for measurement of the peroxide over a two-month period. The peroxide values obtained (Table 4) which reflect shelf life were compared with the predicted shelf life calculated from the results of the FRG-OB (Table 3).

TABLE 3

Induction times of antioxidant treated mayonnaise measured with FRG-OB

| | FRG-OB Induction Time | | |
|---|---|---|---|
| Sample | Induction Time (h) | Standard Deviation (h) | Relative Error (%) |
| control | 57.3 | ±1.4 | 2.4 |
| 750 ppm Fortium R20 | 73.8 | ±2.2 | 2.9 |
| 75 ppm EDTA | 74.3 | ±2.9 | 3.9 |

TABLE 4

Evolution of the peroxide values (mmol/kg) of antioxidant treated mayonnaise in function of time

| | Treatment | |
|---|---|---|
| Day | 750 ppm rosemary extract | 75 ppm EDTA |
| 13 | 6.49 | 7.23 |
| 33 | 9.40 | 9.99 |
| 58 | 21.74 | 19.43 |

A comparison of Tables 3 and 4 shows that the FRG-OB method can successfully predict that the antioxidant EDTA can be replaced with a rosemary extract. The two treatments show equal improvement of the induction times in comparison with the control sample. The non-accelerated shelf life study using peroxide values also indicated this comparable activity for both antioxidants.

The good predictability of shelf life in emulsions can be ascribed to the similarity between the accelerated oxidation conditions and the natural oxidation process. The initiator only produces radicals in the lipid phase and has no influence on the aqueous phase. This is a situation that relates to the natural oxidation process, where the majority of the radical reactions arise in the lipid phase. Apolar azo-initiators, such as 2,2'-azobis(2,4-dimethylvaleronitrile) (AMVN), are known to generate radicals in the lipid phase only (Massaeli, H.; Sobrattee, S.; Pierce, G. N. The Importance of Lipid Solubility in Antioxidants and Free Radical Generating Systems for Determining Lipoprotein Peroxidation. Free Radic. Biol. Med. 1999 1524-1530; Noguchi, N.; Yamashita, H.; Gotoh, N.; Yamamoto, Y.; Numano, R.; Niki, E. 2,2'-Azobis (4-methoxy-2,4-dimethylvaleronitrile), a New Lipid-soluble Azo Initiator: Application to Oxidations of Lipids and Low-Density Lipoprotein in Solution and Aqueous Dispersions. Free Radic. Biol. Med. 1998, 259-268). Krainev et al were able to prove with an EPR experiment that none of the AMVN-derived radical species can escape from the hydrophobic lipid environment (Krainev, A. G.; Bigelow, D. J. Comparison of 2,2'-azobis(2-amidinopropane) hydrochloride (AAPH) and 2,2'-azobis(2,4-dimethylvaleronitrile) (AMVN) as Free Radical Initiators: A Spin-trapping Study. J. Chem. Soc. Perkin Trans. 2. 1996, 747-754). This avoids the formation of reactive oxygen species that can be considered artificial compared to the natural process, enhancing the correlation with the real shelf life of the emulsion Experiment 5—Shelf Life Prediction of Antioxidant Treated Minced Pork Accelerated evaluation of raw meat is impossible when high temperatures are used. The raw meat will start to cook and the original food matrix will modify dramatically due to coagulation of the proteins, denaturation of the iron containing methmyoglobin (prooxidant), and destruction of enzyme activity. These problems will not occur during FRG assays at 40° C.

The correlation between FRG-OB data of antioxidant treated minced pork and the non-accelerated shelf life evaluated with TBARS was investigated. For this purpose three groups of meat samples were evaluated: (1) negative control without antioxidant; (2) treatment with 1000 ppm mixed tocopherols; and (3) treatment with 1000 ppm Fortium® R20 Liquid. Identical samples were also produced without initiator and stored at 6° C. The TBARS content was measured over a period of 11 days. The TBA values which are an indication for the rancidity of the meat samples were compared with the predicted shelf life calculated from the results obtained with FRG-OB.

Figure 8:
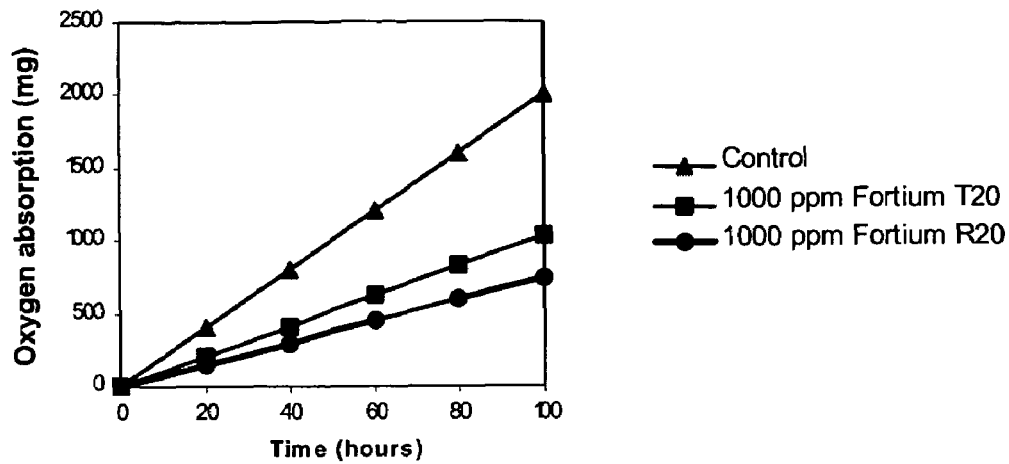
FIG. 8 is a chart of linear regression curves of oxygen absorption over time for a control substrate and the substrate treated with two antioxidant treatments.
Figure 9:
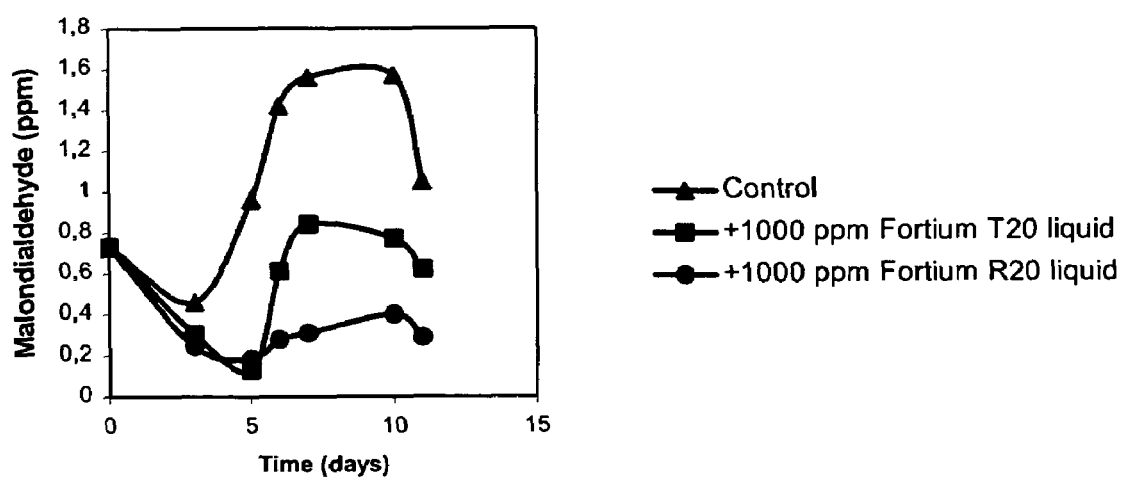
FIG. 9 is a chart of the evolution of thiobarbituric acid (TBA) value as a function of time for a control substrate and the substrate treated with two antioxidant treatments.

The slopes obtained after linear regression of the FRG-OB curves (R2>0.98) shown in FIG. 8 are proportional to the rate of the oxidation reaction and therefore are useful to predict other parameters, which are also proportional to the rate of oxidation (e.g. malondialdehyde). The total surface beneath the TBA-curves of FIG. 9 is a measure of the total amount of malondialdehyde produced during the oxidation.

The slopes of the FRG-OB assays were used to predict the expected TBA maximum, as this gives a very good approximation, of the surface. The slopes for the different treatments indicate that the control sample oxidizes about twice as fast as the sample treated with tocopherols. The treatment with rosemary extract is a clearly the most potent antioxidant. When the maximal TBA value of the control sample is taken as a starting value, it is possible to use the FRG-OB results to estimate the TBA-value of the two treatments. The slope of the control FRG-OB curve with a value of 0.334 corresponds to a TBA value of 1.57. Theoretically the maximal TBA value that would correspond to the slope of 0.172 for the tocopherol-treated sample can be calculated proportionally.

The results from Table 5 show that it is possible to accurately qualify the performance of the antioxidants based on the FRG-OB measurements. Also quantitatively the TBARs give a good correlation with the experimental values. The slightly lower correlation for the rosemary extract-treated sample may be due to the relatively low TBA values and the increased relative error for these smaller experimental values. Overall the FRG-OB is seen to be a valuable method for identification and selection of antioxidant candidates. In combination with known oxidation parameters of the control sample it is also possible to predict the effect of antioxidants on the final shelf life of the analyzed product

TABLE 5

Prediction of TBA values from FRG-OB results.

| Sample | Slope in FRG-OB | Experimental TBA maximum | Predicted TBA maximum |
| --- | --- | --- | --- |
| Control | 0.334 | 1.57 | |
| +1000 ppm Fortium ® T20 Liquid | 0.172 | 0.84 | 0.81 |
| +1000 ppm Fortium ® R20 Liquid | 0.124 | 0.40 | 0.58 |

DISCUSSION

In conclusion, FRG-assays are a valuable alternative to high temperature accelerated oxidation methods. The free radicals produced by AMVN react immediately with unsaturated fatty acids to produce thermodynamically more stable radicals. The oxidation process proceeds much faster than in non-accelerated studies, whilst the disadvantages of heating food or feed samples are circumvented. The time of analysis for soybean oil was reduced from about 24 days in the traditional OSI assay at 50° C. to 24 hours in the FRG-OSI. The main asset of FRG-assays is the improved ability to rapidly compare the qualitative performance of several antioxidants in an accelerated test. Several important weaknesses of traditional accelerated methods are no longer present. First of all the original status of the food matrix is retained easily because of the low temperatures used. Frankel et al identified this as one of the most critical factors for antioxidant evaluation in food (Frankel, E. N.; Meyer, A. Review: The Problems Using One-Dimensional Methods to Evaluate Multifunctional Food and Biological Antioxidants. J. Sci. Food. Agric. 2000, 1925-1941). The new assays also allow the study of antioxidants with low thermal stability without the risk of degradation. Because the analyses can be carried out at temperatures as low as 40° C. or less it is also possible to retain enzyme activity in food products. This may be an important feature in specific products where residual enzymes e.g. peroxidases or lipoxygenases play a role in the oxidation process (Chen, Q.; Shi, H.; Ho, C.-T. Effects of Rosemary Extracts and Major Constituents on Lipid Oxidation and Soybean Lipoxygenase Activity. J. AM; Oil Chem. Soc. 1992, 999-1002; Eriksson, C. E. Lipid Oxidation Catalysts and Inhibitors in Raw Materials and Processed Foods. Food. Chem. 1982, 3-19). Furthermore also changes in antioxidant activity in function of temperature are no longer relevant when the accelerated analyzes are performed at temperatures close to the actual storage temperature. This is important for many antioxidants that exhibit a change in activity at higher temperatures (Gordon, M. H.; Mursi, E. A Comparison of Oil Stability Based on the Metrohm Rancimat with Storage at 20° C. J. Am. Oil Chem. Soc. 1994, 649-651; Tian, K.; Dasgupta, P. K.; Shermer, W. D. Determination of Oxidative Stability of Lipids in Solid Samples. J. Am. Oil Chem. Soc. 2000, 217-222). It was observed for rosemary extracts that the antioxidant efficacy is reduced at higher temperatures and that consequently the antioxidant performance can be underestimated with conventional accelerated techniques.

Until that time the FRG-assays can readily be used as an alternative for traditional analytical methods. The technique is a valuable tool in antioxidant research for a rapid selection of promising antioxidant formulations, or for initial screening of large libraries of antioxidant molecules from botanical sources for their antioxidant effect in food systems.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. A method of measuring the effectiveness of an exogenous antioxidant compound in extending the shelf life of lipid-containing food substrate, comprising the steps of:
   (a) adding an exogenous antioxidant compound to a lipid-containing test food substrate;
   (b) adding a diazo-type free radical source to the substrate in an amount between about 0.01 and about 2 percent by weight of the substrate;
   (c) heating to a temperature not greater than about 70° C.; and
   (d) measuring the efficacy of the antioxidant compound in extending the shelf-life of the test food substrate by comparing products of oxidation produced as a result of treating said food substrate according to steps (a)-(c) with the same products of oxidation produced in a control lipid-containing food substrate treated in the same way as the test substrate but without an exogenous antioxidant.

2. The method of claim 1, wherein the substrate is selected from the group consisting of human food and animal feed products.

3. The method of claim 1, wherein the diazo-type free radical source is selected from the group consisting of compounds which decompose on heating to a temperature not greater than about 70° C. into one or more free radicals.

4. The method of claim 3, wherein the diazo-type free radical source is selected from the group consisting of 2,2'-azobis(2,4-dimethylpentanenitrile), 2,2-azobis(2,4-dimethyipropanenitrile), and 2,2'-azobis(2,4-dimethylbutanenitrile).

5. The method of claim 1, wherein the temperature is between about 35° C. and about 50° C.

6. A method of measuring the effectiveness of an exogenous antioxidant compound in extending the shelf life of a lipid-containing food substrate, comprising the steps of:
   (a) adding an exogenous antioxidant compound to a lipid-containing test food substrate;
   (b) adding a diazo-type free radical source to the substrate in an amount between about 0.01 and about 2 percent by weight of the substrate;
   (c) heating to a temperature not greater than about 70° C. to produce products of the lipid oxidation process; and
   (d) measuring the efficacy of the antioxidant compound in extending the shelf-life of the test of food substrate by comparing the products of the lipid oxidation process with the same products produced in a control lipid-containing food substrate treated in the same way as the test substrate but without an exogenous antioxidant.

7. The method of claim 6, wherein the substrate is selected from the group consisting of human food and animal feed products.

8. The method of claim 6, wherein the diazo-type free radical source is selected from the group consisting of compounds which decompose on heating to a temperature not greater than about 70° C. into one or more free radicals.

9. The method of claim 8, wherein the diazo-type free radical source is selected from the group consisting of 2,2'-azobis(2,4-dimethylpentanenitrile), 2,2-azobis(2,4-dimethylpropanenitrile), and 2,2'-azobis(2,4-dimethylbutanenitrile).

10. The method of claim 6, wherein the substrate is heated to a temperature between about 35° C. and about 50° C.

11. A method of measuring the efficacy of exogenous antioxidant compounds in protecting a lipid-containing food substrate against lipid oxidation processes, comprising the steps of:
   (a) dividing the substrate into at least a first portion and a second portion and adding an antioxidant compound only to the first portion of the substrate;
   (b) adding a diazo-type free radical source to the first and second substrate portions in an amount between about 0.01 and about 2 percent by weight of the substrate;
   (c) heating the first and second substrate portions to a temperature not greater than about 70° C. to produce products of the lipid oxidation process;
   (d) measuring the products of the lipid oxidation process of both portions; and;
   (e) comparing the measurements of the products of the lipid oxidation process of the second portion to those of the first portion in order to measure the efficacy of the antioxidant compound.

12. The method of claim 11, wherein the substrate is selected from the group consisting of human food and animal feed products.

13. The method of claim 11, wherein the diazo-type free radical source is selected from the group consisting of compounds which decompose on heating to a temperature not greater than about 70° C. into one or more free radicals.

14. The method of claim 13, wherein the diazo-type free radical source is selected from the group consisting of 2,2'-azobis(2,4-dimethylpentanenitrile), 2,2-azobis(2,4-dimethylpropanenitrile), and 2,2'-azobis(2,4-dimethylbutanenitrile).

15. The method of claim 11, wherein the temperature is between about 35° C. and about 50° C.

* * * * *